United States Patent [19]

Fruehwirth

[11] Patent Number: Plant 7,231

[45] Date of Patent: May 15, 1990

[54] POINSETTIA PLANT '221'

[75] Inventor: Franz Fruehwirth, Encinitas, Calif.

[73] Assignee: Paul Ecke Ranch, Inc., Encinitas, Calif.

[21] Appl. No.: 263,497

[22] Filed: Oct. 27, 1988

[51] Int. Cl.[5] ..... A01H 5/00
[52] U.S. Cl. ..... Plt./86
[58] Field of Search ..... Plt./86

[56] References Cited

U.S. PATENT DOCUMENTS 4,724,276 2/1988 Ecke, Jr. ..... 800/1

*Primary Examiner*—James R. Feyrer
*Attorney, Agent, or Firm*—Arnold, White & Durkee

[57] ABSTRACT

Described is new Poinsettia cultivar, designated '221', of medium height, having self-branching traits which enhance its value as a flowing branched plant. '221' is particularly distinguished by its large, attractive peppermint colored bracts, comprised of a pink base color, with small, uniformly scattered red flecks.

1 Drawing Sheet

BACKGROUND OF THE INVENTION

'221' is a Poinsettia plant of medium height and large attractive peppermint colored flower bracts. Pink is the base bract color with small red flecks uniformly scattered over the bracts. The plant has self-branching traits which increases its value as a flowering branched plant.

This new Poinsettia cultivar originated as a seedling in a greenhouse in Encinitas, Calif. It was selected because of traits which distinguish it from other Poinsettia cultivars and seems to make it a desirable plant for commercial greenhouse production. This cultivar has a distinct and unusual flower bract color, unlike any Poinsettia presently in commercial greenhouse production. The small flecks of red give a blush to the pink background color. On close inspection this unique color-combination has also been described as a "peppermint" color. After selection, vegetatively reproduction of this plant by stem cuttings for test purposes in Encinitas, Calif., and clones of the plant were subjected to successive generations of vegetative propagation. The bract colors and the percentage of each color of the flower bracts remain stable from generation to generation.

DESCRIPTION OF THE PHOTOGRAPHS

'221' is illustrated in the accompanying color photographs. The upper photo is a side view of a branched plant in full flower. The lower photo is a top view of a plant showing flower and bract formation.

DESCRIPTION OF THE PLANT

The following is a detailed description of this new Poinsettia as observed in a greenhouse in Encinitas, Calif., during December, 1987. Recorded observationsfrom flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Seedling from cross-pollination, the seedling being further treated by the process described in U.S.

Pat. No. 4,724,276, to impart self-branching characteristics thereto.

Classification:

*Botanic.*—*Euphorbia pulcherrima* Willd.
*Common name.*—Poinsettia
*Cultivar name.*—'221'.

Form: Shrub.

Height: Medium.

Growth habit: As a single stemmed plant, upright and vigorous. In full flower, the stem is terminated by a large inflorescence, with several smaller flowering side shoots lower on the stem. Observation of 3 plants in a pot with an overall height of 44 cm. and an overall width of 54 cm. were made. The bract diameter of individual flowers was 34–36 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about nine weeks under continuous long night conditions and night temperatures of about 16–18 degrees C.

Foliage; The foliage is clean and uniformly green from bottom to top of the plant. The leaves are of medium size, leaf blades typically being about 13–15 cm. long and about 7–9 cm. wide with leaf petioles about 4–5 cm. long.

Leaf shape: Typical leaves are ovate with obtuse bases and acuminate tips. Leaf margins are mostly entire with slightlobing or a few minor indentations on each side of the blade.

Color:

*Upper side.*—Darker than R.H.S. 147A.
*Under side.*—Near R.H.S. 138B.

Retention: The foliage retention is good even under low light intensities in the consumer's home.

Bracts: Generally there are 25–28 bicolored pink with red flecked bracts of various sizes subtending the cyathia. The primary bracts have blades typically 16–18 cm. long and 8–10 cm. wide with petioles about 3–4 cm. long.

Shape: Bracts are ovate with acute bases and acuminate tips. Primary bracts are mostly entire with some slight lobing.

Color: Bracts are of a yellow-green ground color (near R.H.S. 145C) as is the bract venation (near R.H.S. 145). Upper bract surfaces between veins is generally uniformly covered by a pink blush(near R.H.S. 38B) which may be lighter near bract margin, stem and tip ends. Bracts are haphazardly flecked with red flecks (near R.H.S. 53B) over their entire upper surface; with flecks being nonuniform in size and shape. The mid-vein on the upper surface of the bracts is overlaid with a thin green line the length of the bract (near R.H.S. 141A). The underside of the bracts — pink blush near R.H.S. 49B, red flecks near R.H.S. 53C.

Cyathia: Generally 12–15 cyathia (flowers (flowers) develop when the plant is in "full bloom". Each cyathium is about 7–8 mm long and about 5–6 mm wide, light green in color, and fringed with a creamy yellow color at the distal end. Usually, one bright yellow nectar cup protrudes from the side of the cyathium. The flower pedicel is also light green and about 6–7 mm in length.The anthers protruding from the cyathia are white.

What is claimed:

1. A new and distinct Poinsettia cultivar, substantially as herein shown and described, distinguished by its peppermint colored flower bracts, comprised of a pink base color with small, uniformly scattered, red flecks.

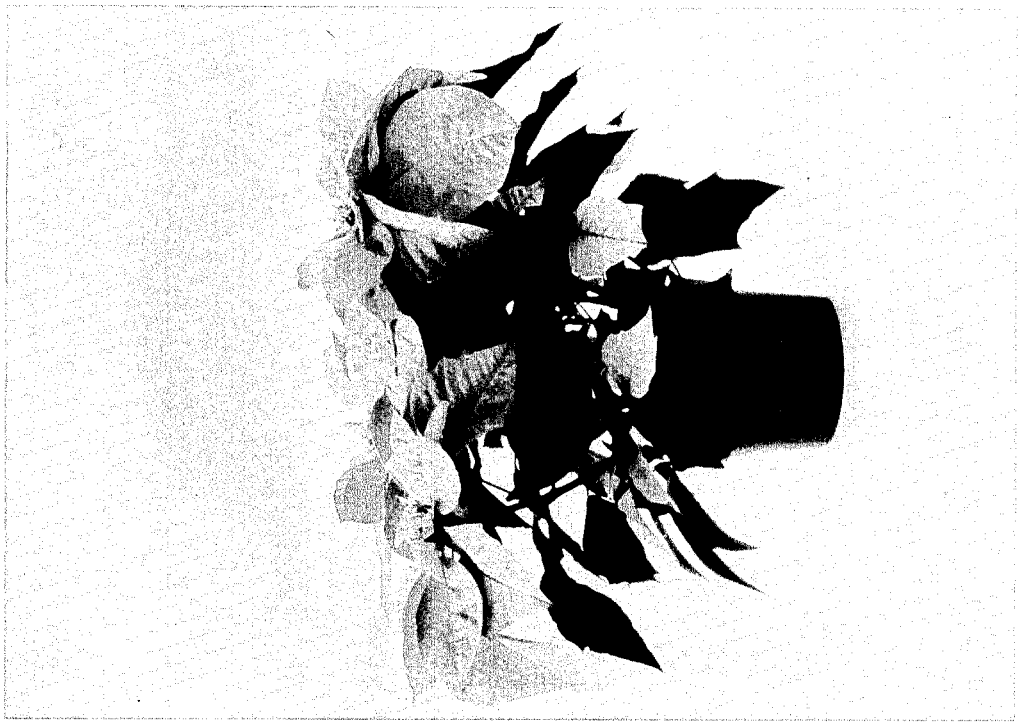
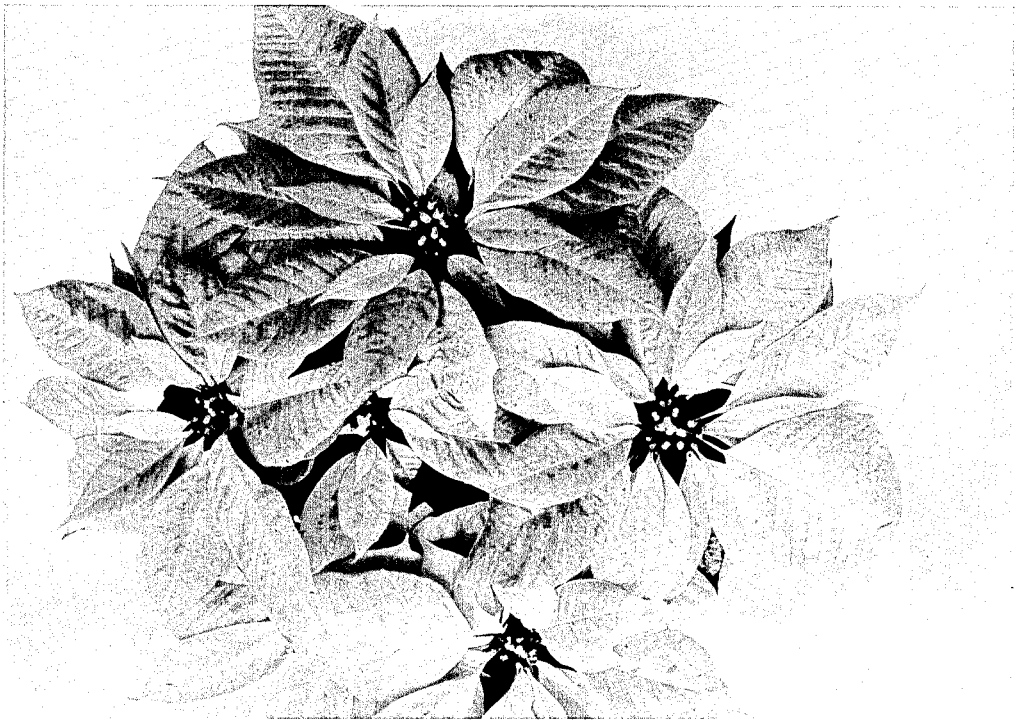

* * * * *